(12) United States Patent
Tokita (10) Patent No.: US 9,043,167 B2
(45) Date of Patent: May 26, 2015

(54) SUBJECT INFORMATION ACQUISITION APPARATUS AND SUBJECT INFORMATION ACQUISITION METHOD

(75) Inventor: Toshinobu Tokita, Yokohama (JP)

(73) Assignee: Canon Kabushiki Kaisha, Tokyo (JP)

( * ) Notice: Subject to any disclaimer, the term of this patent is extended or adjusted under 35 U.S.C. 154(b) by 565 days.

(21) Appl. No.: 13/419,762

(22) Filed: Mar. 14, 2012

(65) Prior Publication Data

US 2012/0239318 A1   Sep. 20, 2012

(30) Foreign Application Priority Data

Mar. 17, 2011   (JP) ................................. 2011-058661

(51) Int. Cl.
*A61B 5/00* (2006.01)
*A61B 8/08* (2006.01)
*A61B 8/00* (2006.01)

(52) U.S. Cl.
CPC .............. *A61B 8/0825* (2013.01); *A61B 5/0091* (2013.01); *A61B 5/0095* (2013.01); *A61B 8/403* (2013.01)

(58) Field of Classification Search
CPC ...................................................... A61B 5/0091
USPC .......................................................... 702/56
See application file for complete search history.

(56) References Cited

U.S. PATENT DOCUMENTS

| 6,607,489 B2 | 8/2003 | Hoctor | |
| 2005/0240101 A1* | 10/2005 | Kato et al. | 600/437 |
| 2012/0238858 A1* | 9/2012 | Tokita | 600/407 |

FOREIGN PATENT DOCUMENTS

JP   2010-17427 A   1/2010

OTHER PUBLICATIONS

Srirang Manohar, et al., The Twente photoacoustic mammoscope: system overview and performance, Physics in Medicine and Biology 50 (2005) 2543-2557.

* cited by examiner

*Primary Examiner* — Bryan Bui
(74) *Attorney, Agent, or Firm* — Canon USA Inc. IP Division

(57) ABSTRACT

A subject information acquisition apparatus includes a first holding member that holds a subject, a probe that receives an elastic wave from the subject through the first holding member, a first holding member deformation amount measuring unit that measures an amount of deformation of the first holding member, and a processing unit that creates an area for generating subject information by using the amount of deformation of the first holding member and position information of the first holding member deformation amount measuring unit and generates an information value of subject information corresponding to the area for generating subject information by using a signal outputted by the probe.

10 Claims, 10 Drawing Sheets

SUBJECT INFORMATION ACQUISITION APPARATUS AND SUBJECT INFORMATION ACQUISITION METHOD

BACKGROUND OF THE INVENTION

1. Field of the Invention

The present invention relates to a subject information acquisition apparatus and a subject information acquisition method for acquiring subject information of a subject by receiving an elastic wave. In this description, the elastic wave is a concept including a sound wave, an ultrasonic wave, an acoustic wave, a photoacoustic wave, and an optical ultrasonic wave.

2. Description of the Related Art

Photoacoustic imaging (PAI) attracts attention as a method for specifically imaging angiogenesis caused by cancer. The photoacoustic imaging is a method for irradiating illumination light (near-infrared light or the like) to a living organism or the like and receiving photoacoustic waves generated from the inside of the living organism by a probe to make an image. As a method for acquiring an image inside a living organism by using a principle of the photoacoustic imaging, photoacoustic mammography (PAM), whose subject is a breast, is disclosed in Srirang Manohar, et al., The Twente photoacoustic mammoscope: system overview and performance, Physics in Medicine and Biology 50 (2005) 2543-2557.

Figure 4A:
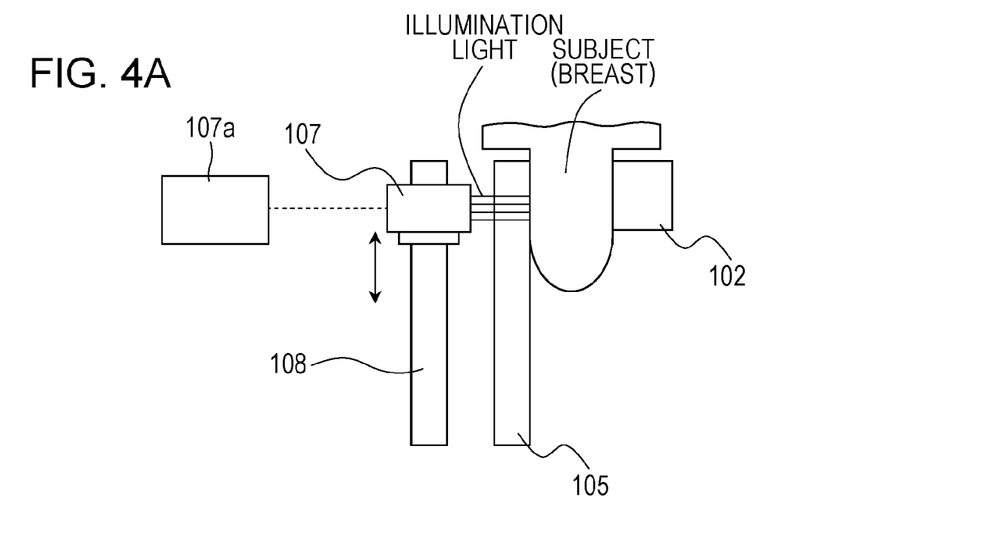
FIGS. 4A to 4C are diagrams for explaining a related art.

FIG. 4A is a schematic side view of a measuring method of the above document. In FIG. 4A, an Nd:YAG laser 107a is a light source that illuminates the subject (breast). An illumination optical system 107 guides laser light emitted from the Nd:YAG laser 107a to the subject and illuminates the subject. An illumination system scanning mechanism 108 includes the illumination optical system 107 and causes the illumination optical system 107 to scan in a vertical direction (a direction indicated by an arrow in FIG. 4A) and a horizontal direction (a direction perpendicular to the page of FIG. 4A). The probe 102 receives a photoacoustic wave generated from the subject. A signal processing unit not shown in FIG. 4A selects a receiving device of the probe 102 that acquires a signal to form an image from an illumination position set by the illumination system scanning mechanism 108, amplifies the signal, converting the signal into a digital signal, and reconstruct the image. A holding plate 105 made of glass transmits illumination light from the illumination optical system 107 and compresses and holds the subject between the holding plate 105 and the probe 102. A subject person lies on her stomach on a bed not shown in FIG. 4A and inserts her breast, which is the subject, into an insertion hole in the bed. The subject is compressed and held between the probe 102 and the holding plate 105. The apparatus disclosed in the above document acquires image data in a living organism from a photoacoustic signal by a measuring method shown in FIG. 4A.

Figure 4B:
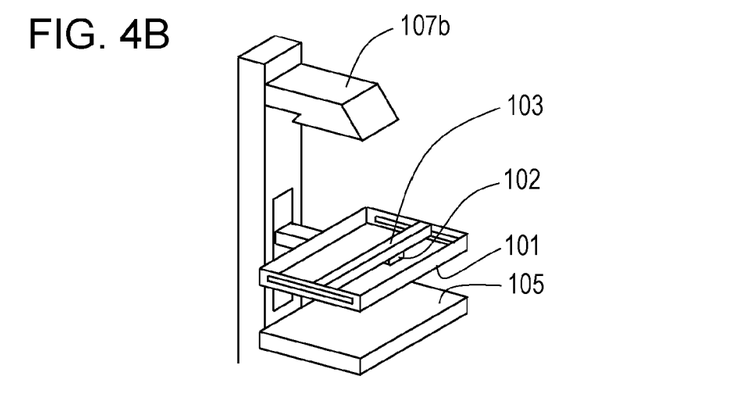

A multifunction device including an X-ray mammography machine and an ultrasonic device as shown in FIG. 4B is disclosed in U.S. Pat. No. 6,607,489. The device shown in FIG. 4B compresses and holds a subject not shown in FIG. 4B between a first holding plate 101 and a second holding plate 105 by moving the first holding plate 101. A small probe 102 which can move along a surface of the first holding plate 101 is provided on the first holding plate 101 on the opposite side of the subject. The probe 102 is held by a gantry 103 which functions as a guide. The probe 102 transmits an ultrasonic wave to the subject through the first holding plate 101. The device shown in FIG. 4B acquires an ultrasonic image in the subject by using a signal generated from a wave reflected from the subject and received by the probe 102.

However, as disclosed in U.S. Pat. No. 6,607,489 and Srirang Manohar, et al., The Twente photoacoustic mammoscope: system overview and performance, Physics in Medicine and Biology 50 (2005) 2543-2557, in elastic wave imaging in which an elastic wave is received and the subject information is acquired from a received signal while the subject is held by the plates, it is desired that the image quality is further improved.

SUMMARY OF THE INVENTION

In the elastic wave imaging in which the subject information is acquired while the subject is held by the plates, an aspect of the present invention provides a subject information acquisition apparatus and a subject information acquisition method for acquiring a higher quality image.

An aspect of the present invention provides a subject information acquisition apparatus including a first holding member that holds a subject, a probe that receives an elastic wave from the subject through the first holding member, a first holding member deformation amount measuring unit that measures an amount of deformation of the first holding member, and a processing unit that creates an area for generating subject information by using the amount of deformation of the first holding member and position information of the first holding member deformation amount measuring unit and generates an information value of subject information corresponding to the area for generating subject information by using a signal outputted by the probe.

In light of the above described aspect, it is possible to provide a subject information acquisition apparatus and a subject information acquisition method for acquiring a higher quality image in the elastic wave imaging in which the subject information is acquired while the subject is held by plates.

Further features of the present invention will become apparent from the following description of exemplary embodiments with reference to the attached drawings.

DESCRIPTION OF THE EMBODIMENTS

In elastic wave imaging, it is necessary to create an area (reconstruction area) for generating subject information to generate an image of the subject information by using a signal outputted when a probe receives an elastic wave.

Therefore, a creation method of the reconstruction area studied by the inventors of the present invention will be described with reference to a subject information acquisition apparatus shown in FIGS. 5A and 5B.

Figure 5A:
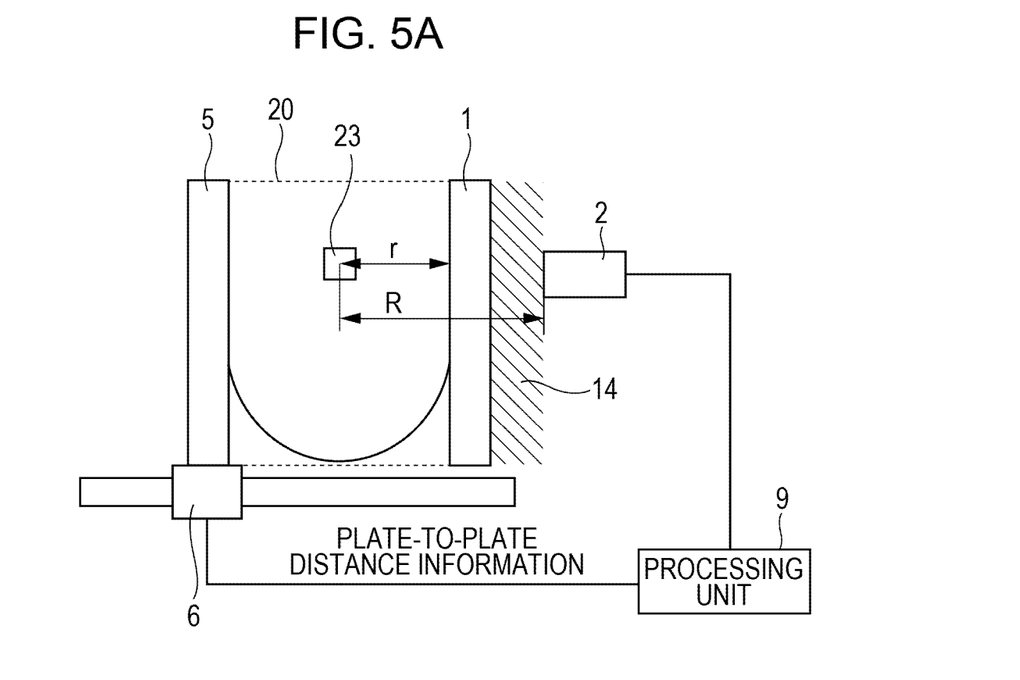
FIGS. 5A and 5B are diagrams for explaining a creation method of a reconstruction area studied by the inventors of the present invention.

The subject information acquisition apparatus shown in FIG. 5A acquires subject information while sandwiching a subject by two plates (a first holding plate and a second holding plate). Here, a probe 2 receives an elastic wave in a state in which a matching material 14 is filled between the probe 2 and the first holding plate 1.

At this time, a processing unit 9 sets a distance between the plates, which is measured by a compression mechanism 6, as a width of a reconstruction area 20 in a horizontal direction on the page. The processing unit 9 sets a receiving range (scanning range) of the probe 2 as a width of the reconstruction area 20 in a vertical direction on the page.

Figure 5B:
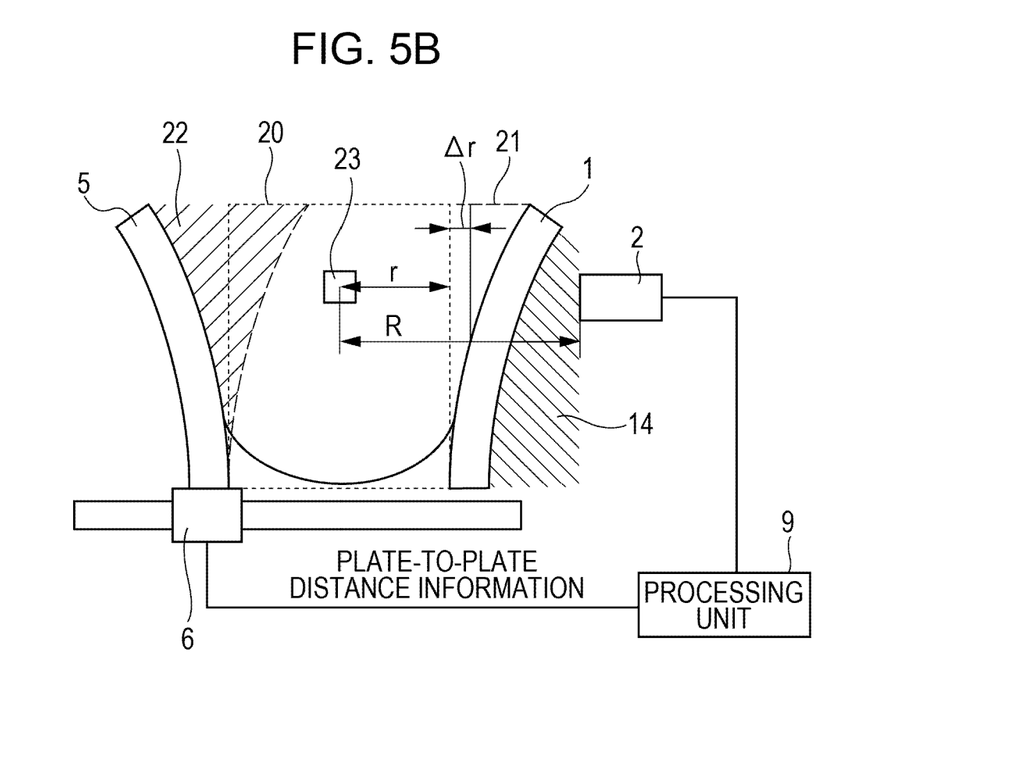

However, when the two plates sandwich the subject, as shown in FIG. 5B, the plates may deform toward the outside.

In this case, the shape of the reconstruction area 20 is different from the shape of the subject because the distance between the plates is set as the width of the reconstruction area 20 in the horizontal direction on the plate. Therefore, only the subject information of the subject in a position of a subject information acquisition area 21 corresponding to the reconstruction area 20 is made into an image. In other words, there is a blind area 22 in which image information is not generated even though the subject is present, so that the entire object cannot be made into an image.

Let us consider a case in which the probe 2 receives an elastic wave through the first holding plate 1 as shown in the subject information acquisition apparatus in FIG. 5B. In this case, the shape of the reconstruction area 20 near the first holding plate 1 is different from the shape of the subject, so that it is impossible to correctly estimate a distance which an elastic wave propagates in the subject. As a result, the resolution of the image of the subject information degrades.

Specifically, in the reconstruction area 20 in which the deformation of the plates is not considered, a time period during which an elastic wave propagates from a point of interest 23 to the probe 2 is calculated by defining a distance which the elastic wave propagates in the subject as r. However, when the first holding plate 1 is deformed, the distance which the elastic wave actually propagates in the subject is r+Δr. Thereby, the time period which the elastic wave actually propagates in the subject is different from the calculated propagation time, so that it is impossible to accurately extract a signal intensity of a time corresponding to the point of interest 23 from a signal outputted from the probe 2. Therefore, the quantitativity of the subject information at each point of interest degrades. As a result, the resolution of the image of the subject information degrades.

Thus, in view of the problem described above, the inventors hit upon an idea of creating an area for generating the subject information by considering the amount of deformation of the plates.

The subject information acquisition apparatus of the present invention includes an apparatus that uses an ultrasonic pulse-echo technique in which an ultrasonic wave is transmitted to a subject, an ultrasonic wave reflected in the subject is received, and subject information is acquired as image data (image information) or the like. The subject information acquisition apparatus also includes an apparatus that uses a photoacoustic effect in which a subject is irradiated with light (electromagnetic wave), an elastic wave (typically, an ultrasonic wave) generated in the subject is received, and subject information is acquired.

In the former apparatus which uses the ultrasonic pulse-echo technique, the acquired subject information is information in which differences of acoustic impedances of tissues in the subject and the like are reflected. In the latter apparatus which uses the photoacoustic effect, the acquired subject information is a generation source distribution of the elastic waves generated by irradiation of light, an initial acoustic pressure distribution in the subject, a light energy absorption density distribution derived from the initial acoustic pressure distribution, an absorption coefficient distribution, and a density distribution of material included in the tissues and the like. The density distribution of material is, for example, a distribution of degrees of oxygen saturation and an oxyhemoglobin/deoxyhemoglobin density distribution.

In the present invention, the components described below can be used as components of the embodiments described later.

(Probe)

The probe receives an elastic wave generated or reflected in the subject. A receiver of the probe has one or more conversion devices that receive an elastic wave and convert the elastic wave into an electric signal. The receiver includes a conversion device that uses a piezoelectric phenomenon, a conversion device that uses an optical resonation, and a conversion device that uses capacitance change, and the like. As the receiver of the probe, any receiver that can receive an elastic wave and convert the elastic wave into an electrical signal can be used. A plurality of conversion devices that receive an elastic signal are one-dimensionally or two-dimensionally arranged, so that an elastic wave can be received at a plurality of places at the same time. Thus, it is possible to shorten a reception time and reduce effects of vibration and the like of the subject. When a probe scanning mechanism causes one conversion device to scan, it is possible to acquire the same signals as those acquired by the conversion devices that are two-dimensionally or one-dimensionally arranged. The conversion devices may be provided on the entire surface of the subject.

The probe receives an elastic wave through a first holding member described later.

(Light Source)

A light source in the apparatus which uses the photoacoustic effect is a unit for irradiating light having a specific wavelength absorbed by a specific component (for example, hemoglobin) included in the subject (living organism or the like). For example, the light source includes at least one pulse light source capable of generating pulse light of 5 to 50 nanoseconds. Although the light source is desired to be a laser having a large output power, a light-emitting diode or the like can be used instead of laser. As the laser, various lasers such as a solid-state laser, a gas laser, a dye laser, a semiconductor laser can be used. The light may be emitted from the side of the probe or may be emitted from the side opposite to the probe. Further, the light may be irradiated to both sides of the subject. Here, the light means an electromagnetic wave including visual light and infrared light.

Specifically, the light means light having a wavelength in a range, for example, from 500 nm to 1300 nm. Light having a specific wavelength within the above range may be selected depending on a component to be measured.

(Illumination System)

Examples of an optical member of the illumination system includes a mirror that reflects light, a lens that collects, enlarges, or deforms light, and a prism that diffuses/refracts/reflects light, an optical fiber that propagates light, and a diffuser panel. The light emitted from the light source can be guided to the subject by optical members such as a lens and a mirror or propagated by an optical member such as an optical fiber. As the optical members, any member can be used if the light emitted from the light source is irradiated to the subject in a desired shape. Generally, the light is desired to be enlarged to a certain area rather than to be collected by a lens in a viewpoint of safety of a living organism and enlargement of diagnostic area. An area irradiated with light in the subject (an irradiation area) is desired to be movable. When the irradiation area is movable, a larger area can be irradiated with light. It is further desired that the irradiation area moves in synchronization with the probe. As a method for moving the irradiation area, there are a method that uses a movable mirror and a method that mechanically moves a light source and an optical member.

(First and Second Holding Members)

A first and a second holding members are members for holding at least a part of the shape of the subject. When the first and the second holding members sandwich the subject, a position of the subject is fixed during the measurement, so that a position error due to movement of the body and the like can be reduced. Further, it is possible to effectively transmit light and an ultrasonic wave to a deep portion in the subject by compressing the subject. As the first and the second holding members, it is possible to use a member having high transmittance of light and ultrasonic wave and high acoustic integrity with the subject and the probe. Polymethylpentene that has an acoustic impedance similar to that of the subject is suitable for the material of the first and the second holding plates.

The first holding member is provided between the subject and the probe and the probe can receive an elastic wave through the first holding member.

An acoustic matching material (matching material) such as gel may be provided between the holding members and the subject and between the holding member and the probe in order to improve acoustic integrity.

(Subject and Light Absorber)

A subject measured by an apparatus that uses a photoacoustic effect will be described. The subject information acquisition apparatus mainly diagnoses malignant tumor, vascular disease, blood sugar level, and the like of a human and an animal and observes processes of chemical treatment. Therefore, a specific subject may be a portion to be diagnosed, such as a breast, a finger, a limb, or the like of a human or an animal. The light absorber is a body having a relatively high absorption coefficient in the subject. For example, when a human body is a target to be measured, the light absorbers are oxyhemoglobin, deoxyhemoglobin, a blood vessel containing oxyhemoglobin and/or deoxyhemoglobin, and a malignant tumor including many newborn blood vessels. The light absorber on the surface of the subject is melanin and the like located near the surface of the skin.

Hereinafter, specific embodiments will be described.

First Embodiment

Figure 1A:
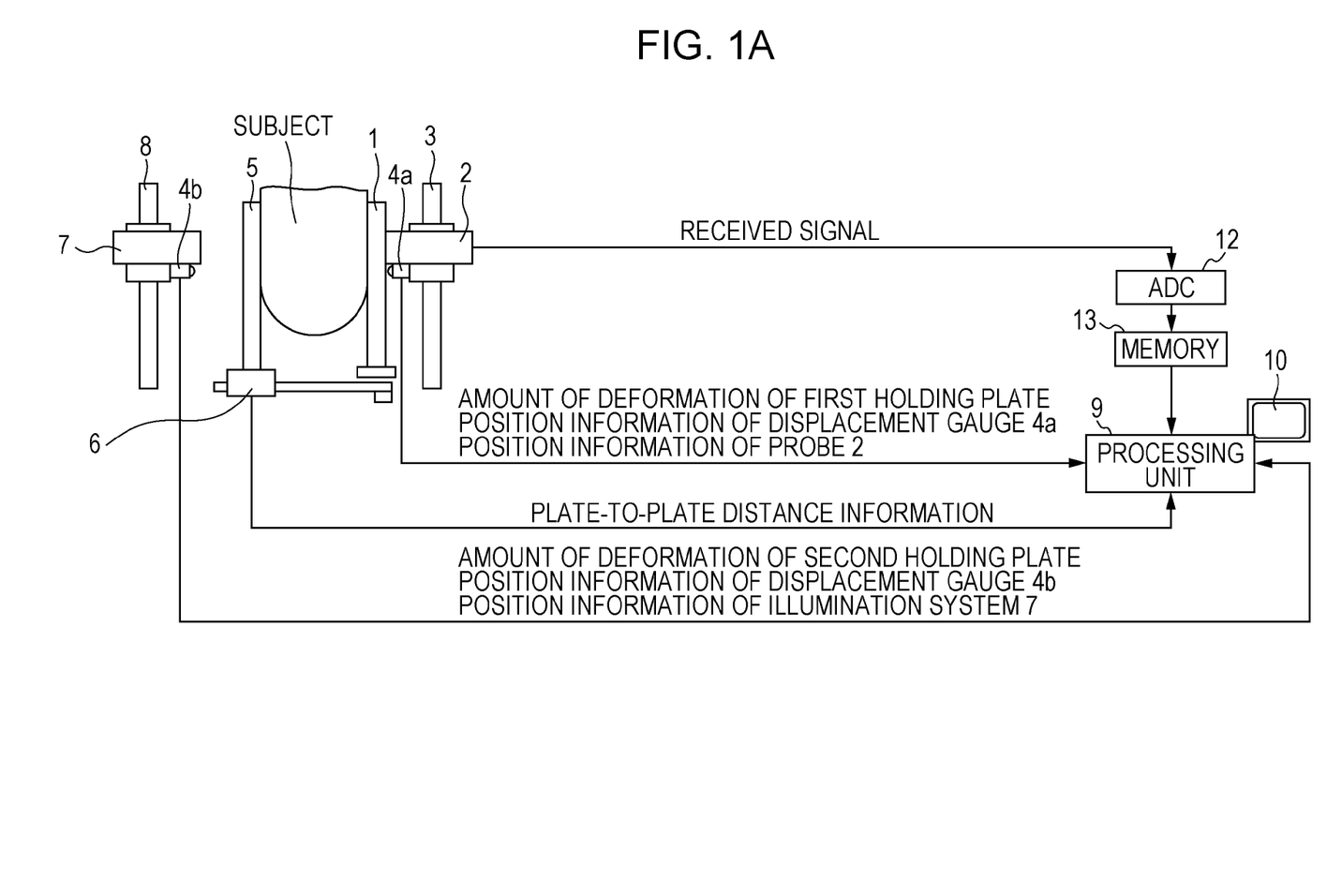
FIGS. 1A to 1C are diagrams for explaining an apparatus configuration and a process method according to a first embodiment of the present invention.

A first embodiment will be described with reference to FIGS. 1A to 1C. FIG. 1A schematically shows a diagram of a photoacoustic apparatus in which a subject (a breast or the like) inserted and sandwiched between a first holding plate 1 and a second holding plate 5 and subject information is measured by using an elastic wave.

The first holding plate 1, which is the first holding member, is to hold the subject.

A probe 2 can receive an ultrasonic wave emitted from the subject through the first holding plate 1 and the probe 2 includes an array of transducer elements. A received signal that is received by the probe 2 is digitally converted by ADC 12 and the digitally converted received signal is stored in a memory 13.

A probe scanning mechanism 3 includes the probe 2 and causes the probe 2 to scan along a surface of the first holding plate 1. A matching material 14 for acoustic matching is filled between the first holding plate 1 and a receiving surface of the probe 2.

The probe scanning mechanism 3 includes a displacement gauge 4a, which is a first holding member deformation amount measuring unit. The displacement gauge 4a measures the amount of outward deformation (displacement information) of the first holding plate 1. A processing unit 9 acquires position information of the displacement gauge 4a and the probe 2 on the basis of a scanning position of the probe scanning mechanism 3.

The displacement gauge 4a may be a contact type gauge using an electric micrometer or the like or a non-contact type gauge using an optical sensor or the like. The displacement gauge 4a can be a unit using a method in which an ultrasonic wave is transmitted to and received from the first holding plate 1 and the amount of deformation of the first holding plate 1 at each scanning position is measured by multiplying the time period between the transmission and the reception by the sound speed in the acoustic matching material.

The second holding plate 5, which is the second holding member, sandwiches the subject between the second holding plate 5 and the first holding plate 1 and compresses and holds the subject by about 10 N to 300 N. The operations for the second holding plate 5 to compress and hold the subject and release the compression are performed by a compression mechanism 6 that drives the second holding plate 5.

An illumination system 7 is an optical system for irradiating near infrared light whose wavelength is about 600 to 1100 nm to the subject through the second holding plate 5. The illumination system 7 is mounted on an illumination system scanning mechanism 8. FIG. 1A does not show the light source and the optical system from the light source to the illumination system 7.

The illumination system scanning mechanism 8 includes a displacement gauge 4b, which is a second holding member deformation amount measuring unit. The displacement gauge 4b measures the amount of outward deformation (displacement information) of the second holding plate 5. A processing unit 9 acquires position information of the displacement gauge 4b and the illumination system 7 on the basis of a scanning position of the illumination system scanning mechanism 8.

Figure 1B:
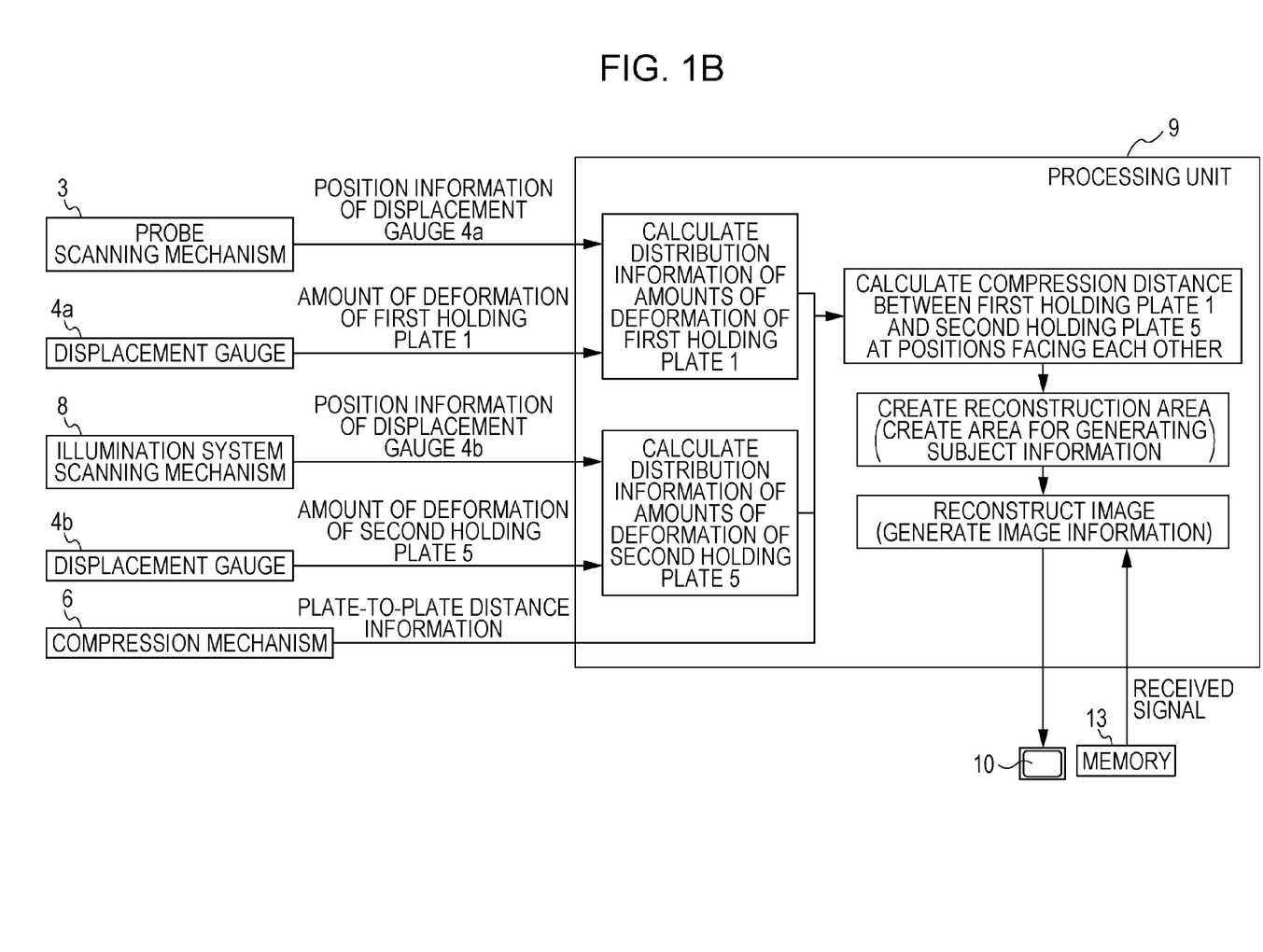
Figure 1C:
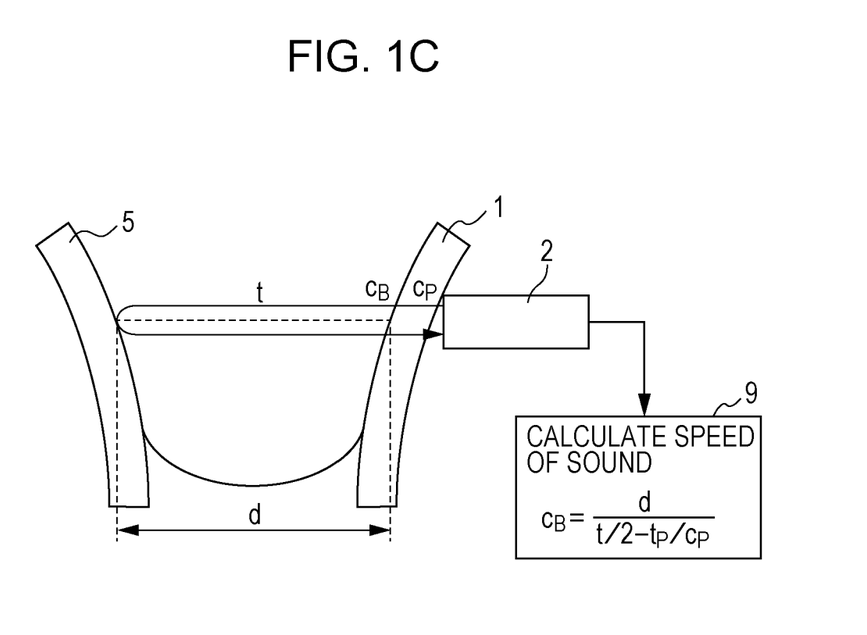

As shown in FIG. 1B, the processing unit 9 obtains distribution information of amounts of deformation of the first holding plate 1 by using the position information of the displacement gauge 4a acquired from the scanning position of the probe scanning mechanism 3 and the amounts of deformation of the first holding plate 1 acquired by the displacement gauge 4a.

The distribution information of amounts of deformation is a degree of deformation from the original shape and indicates information related to one-dimensional or two-dimensional deformation. For example, when the original shape of the first holding plate 1 is a flat plate shape, the distribution information is flatness information.

Similarly, the processing unit 9 obtains distribution information of amounts of deformation of the second holding plate 5 by using the position information of the displacement gauge 4b acquired from the scanning position of the illumination system scanning mechanism 8 and the amounts of deformation of the second holding plate 5 acquired by the displacement gauge 4b.

Then, the processing unit 9 performs a process for calculating a compression distance between the first holding plate 1 and the second holding plate 5 at positions facing each other from the distribution information of amounts of deformation of the first holding plate 1 and the distribution information of amounts of deformation of the second holding plate 5, and plate-to-plate distance information measured by a member-to-member distance measuring unit (for example, a linear scale) provided in the compression mechanism 6.

Next, the processing unit 9 creates a reconstruction area (an area for generating the subject information) from the compression distance between the positions facing each other obtained on the basis of the distribution information of amounts of deformation of the plates.

The processing unit 9 refers to the received signal stored in the memory 13, performs image reconstruction at each point of interest in the reconstruction area, and generates image information. Then, the processing unit 9 displays the image information on a monitor 10.

In this way, it is possible to obtain a correct compression distance between the first holding plate 1 and the second holding plate 5 at positions facing each other by using the distribution information of amounts of deformation of the plates. Therefore, the processing unit 9 can create the reconstruction area with a high degree of accuracy.

Thus, it is possible to acquire the subject information over the entire subject by creating the reconstruction area with a high degree of accuracy considering the deformation of the plates. Specifically, it is possible to make an image of the blind area 22 which is not imaged in FIG. 5B.

Further, a distance which an elastic wave propagates in the subject can be correctly estimated, so that it is possible to accurately extract a signal intensity of a time corresponding to a point of interest from a signal outputted from the probe. Therefore, the resolution of the acquired image can be improved.

When the subject is compressed and held by the first holding plate 1 and the second holding plate 5, the sound speed in the subject changes. To measure the sound speed in the subject, for example, as shown in FIG. 1C, an ultrasonic wave is emitted from the probe 2 and the ultrasonic wave which passes through the first holding plate 1 and the subject and which is reflected by the second holding plate 5 is receive by the probe 2. It can be calculated that (round-trip time of the ultrasonic wave t)/2=(thickness of the first holding plate 1 $t_P$)/(sound speed in the first holding plate 1 $c_P$)+(compression distance d)/(sound speed in the subject $c_B$), so that the sound speed in the subject $c_B$=d/(t/2−$t_P$/$c_P$) can be calculated. At this time, the received signal stored in the memory 13 is referred to in order to obtain the round-trip time of the ultrasonic wave.

In summary, the process performed by the processing unit 9 to generate the subject information can include processes of transmitting an elastic wave from the probe to the subject through the first holding member, receiving the reflected elastic wave through the first holding member, and acquiring the sound speed in the subject by using the distance between the first holding plate 1 and the second holding plate 5 at positions facing each other.

In this way, the sound speed in the subject can be measured with a high degree of accuracy while the subject is held, so that it is possible to reduce degradation of resolution caused by error in calculation of the sound speed.

The compression mechanism 6 may compress the subject by driving the first holding plate 1.

Second Embodiment

A photoacoustic apparatus of a second embodiment is different from the photoacoustic apparatus of the first embodiment and has a configuration in which the subject is compressed onto a first holding plate.

Figure 2A:
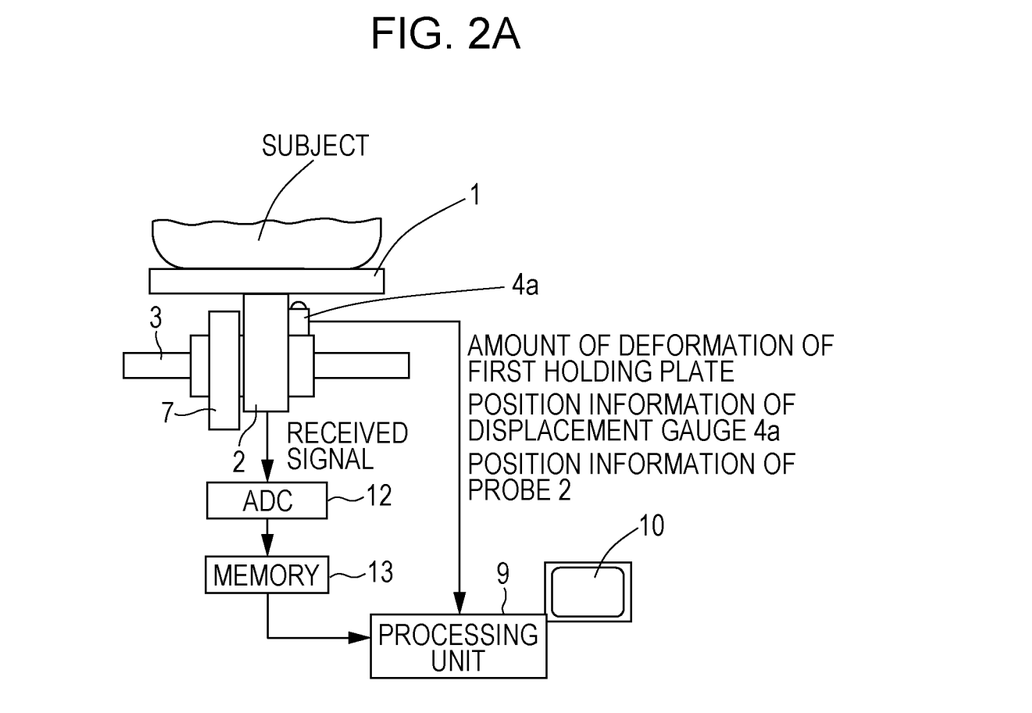
FIGS. 2A to 2C are diagrams for explaining an apparatus configuration and a process method according to a second embodiment of the present invention.

FIG. 2A shows the configuration of the photoacoustic apparatus of the present embodiment. In the photoacoustic apparatus of the present embodiment, the subject is compressed and held onto the first holding plate 1 and near infrared light is irradiated to the subject by an illumination system 7. A probe 2 receives an elastic wave emitted from the subject. A displacement gauge 4a for measuring the amount of deformation of the first holding plate 1, the probe 2, and the illumination system 7 are mounted on the probe scanning mechanism 3.

Figure 2B:
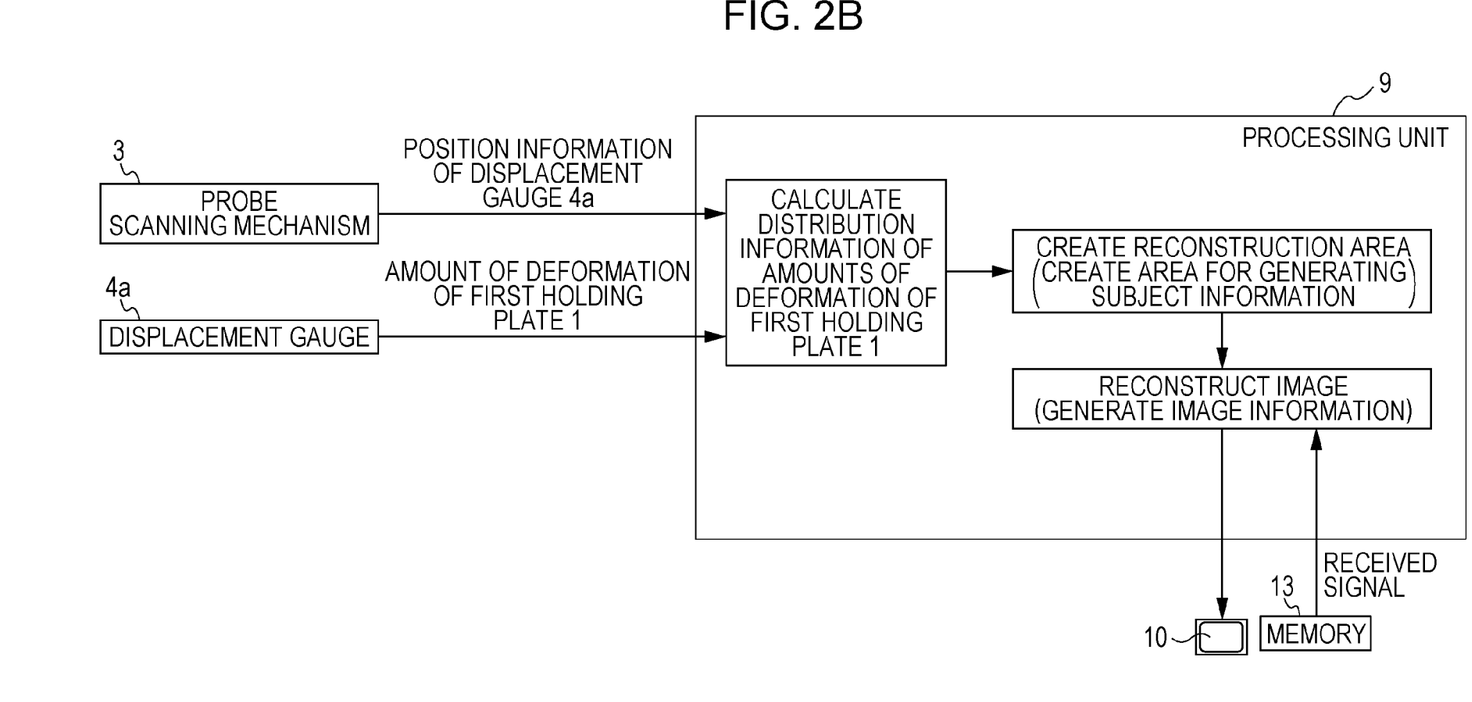

As shown in FIG. 2B, when the subject is held by the first holding plate 1, the processing unit 9 obtains distribution information of amounts of deformation of the first holding plate 1 from position information of the displacement gauge 4a acquired from a scanning position of the probe scanning mechanism 3 and the amounts of deformation of the first holding plate 1 acquired by the displacement gauge 4a.

Then, the processing unit 9 creates a reconstruction area including an interface where the first holding plate 1 and the subject are contact with each other from the distribution information of amounts of deformation of the first holding plate 1.

In this way, the present embodiment has a configuration, in which the subject is not compressed and held, and creates an area for generating image information (the reconstruction area) by using the distribution information of amounts of deformation of the first holding plate 1 that holds the subject.

In the reconstruction area obtained by considering the distribution information of amounts of deformation of the holding plate, at least a reconstruction area near the holding plate is accurate, so that it is possible to correctly estimate a distance which an elastic wave propagates in the subject.

Therefore, it is possible to accurately extract a signal intensity of a time corresponding to each point of interest in the reconstruction area from a signal outputted from the probe, so that the quantitativity of the subject information at a point of interest is high. As a result, according to the present embodiment, the resolution of the image of the subject information can be improved.

Although, in the first embodiment and the second embodiment, the configurations of the photoacoustic apparatuses are described, as described above, the present invention is not limited to a photoacoustic apparatus. Any apparatus in which reception is performed by the probe 2 through the first holding plate 1 can also be applied to an ultrasonic apparatus. It is possible to employ a method in which the image information is generated in real time and displayed on the monitor 10.

Figure 2C:
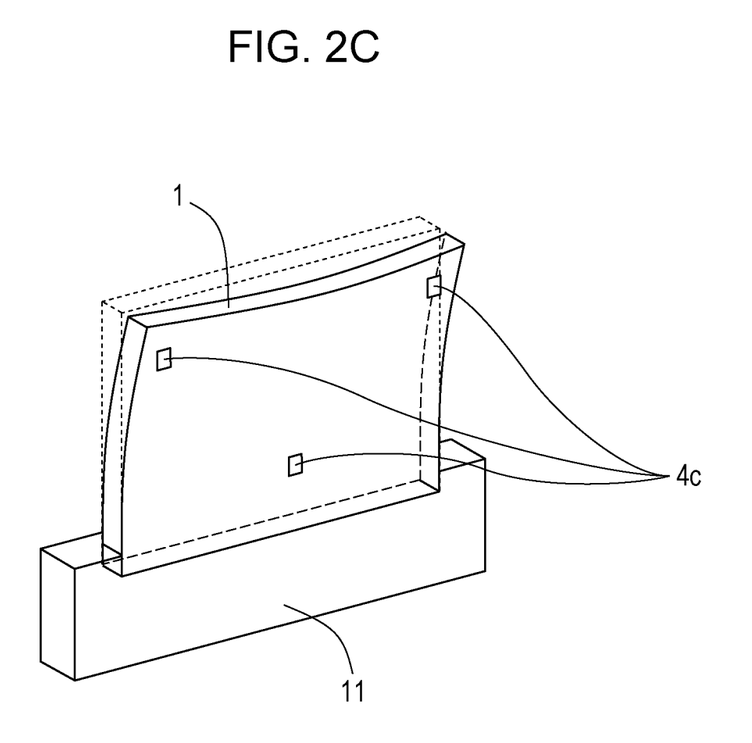

Although measuring methods of contact type and non-contact type are described as methods of the displacement gauge, the measuring method is not limited to these. As shown in FIG. 2C, a strain gauge 4c is attached to a plurality of positions on the first holding plate 1 or a first plate holding member 11 that fixes the first holding plate 1 and the processing unit 9 may obtain the distribution information of amounts of deformation of the first holding plate 1 from outputs of the strain gauges 4c when a load is applied. In this case, the distribution information of amounts of deformation of the first holding plate 1 can be obtained without mounting the strain gauge 4c, which is a first holding member deformation amount measuring unit, on the probe scanning mechanism 3.

Besides the strain gauge 4c, it is possible to use a sensor, which is directly attached to the first holding plate 1 and/or the first plate holding member 11, such as a piezoelectric element, in particular, a piezoelectric film.

In this way, the first holding member deformation amount measuring unit may be a unit which is directly attached to a plurality of positions on the holding member and/or a fixing member that fixes the holding member. Such a first holding member deformation amount measuring unit can be applied to a measuring unit that acquires the distribution information of amounts of deformation of the second holding plate 5 in the first embodiment. In this case, the second holding member deformation amount measuring unit may be directly attached to the second holding plate 5 and/or a second plate holding member that fixes the second holding plate 5.

Further, although, in the first embodiment and the second embodiment, it is described that the first holding plate 1 is a flat plate (has a flat plate shape) when the subject is not held, it is not limited to a flat plate. For example, the first holding plate 1 may have a bowl-shape. In this case, if the flatness and the curvature when the subject is not held are known, the distribution information of amounts of deformation of the first holding plate 1 when the subject is held can be obtained from the amounts of deformation acquired by the displacement gauge 4a and the position information of the displacement gauge 4a.

Third Embodiment

Figure 4C:
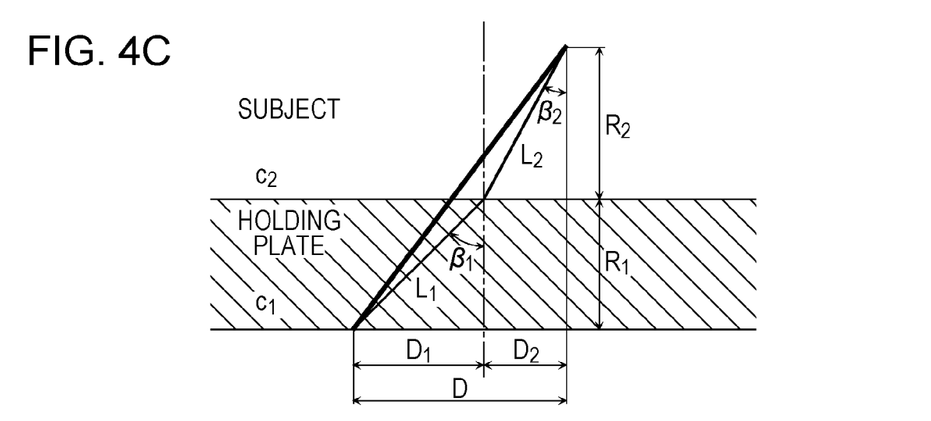

U.S. Pat. No. 6,607,489 discloses a technique for correcting refraction of an elastic wave caused by a difference of the sound speeds in the plate and the subject in ultrasonic imaging shown in FIG. 4C. Specifically, it is described that, to correct refraction of an elastic wave that reaches an element of the probe from a certain point in the subject, a delay time T is calculated using the four formulas described below and a signal from each element of the probe is added ($c_1$ and $c_2$ are sound speeds).

$$T = L_1/c_1 + L_2/c_2$$

$$\beta_1 = \sin^{-1}(c_1/c_2 \times \sin \beta_2)$$

$$T = R_1/(c_1 \cos \beta_1) + R_2/(c_2 \cos \beta_2)$$

$$D = R_1 \tan \beta_1 + R_2 \tan \beta_2$$

The inventors applied the technique for correcting refraction described in U.S. Pat. No. 6,607,489 to the elastic wave imaging that performs image reconstruction.

However, in the subject information acquisition apparatus shown in FIG. 5B, the shape of the reconstruction area 20 is different from the shape of the subject, so that it is impossible to correctly know the shape of the interface between the subject and the holding plate 1 on the basis of the reconstruction area 20. In this case, the processing unit 9 cannot correctly know the incident position and the incident angle of the elastic wave to the holding plate 1, so that if refraction correction is performed by using the reconstruction area 20 created by the method studied by the inventors, the resolution of the image of the subject information degrades.

Therefore, in view of the above problem, the inventors found a method in which the image information is generated by correcting the refraction of the elastic wave in the deformed first holding plate 1 by using the accurate reconstruction area created in the first embodiment or the second embodiment.

Figure 3A:
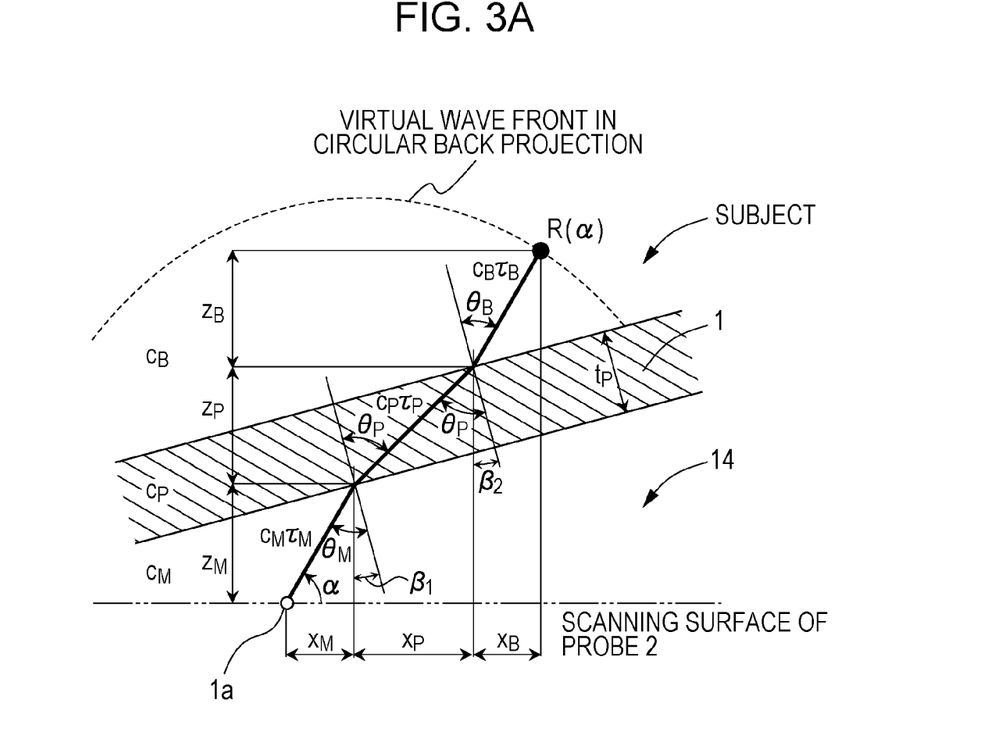
FIGS. 3A and 3B are diagrams for explaining refraction correction of an elastic wave when reconstructing an image according to a third embodiment of the present invention.

Hereinafter, the method for correcting the refraction according to the present embodiment will be described. FIG. 3A shows an outline of an image reconstruction method by a circular back projection method. The circular back projection method will be described below. A time $\tau$ in which an elastic wave emitted from a certain point in the subject reaches one element 2a of a transducer array of the probe 2 is acquired and a virtual wave front is drawn at a distance corresponding to $\tau$ away from the element. The time $\tau$ is a time period from when the light is emitted to when the signal is acquired at the element 2a.

When a virtual wave front is drawn for each element in the same manner, the generation source of the elastic wave can be identified as a position at which the virtual wave fronts overlap. The subject information such as an absorption coefficient distribution can be generated as an image by plotting information values such as absorption coefficients and oxygen saturation values based on a signal of the elastic wave from the generation source at each point of interest in the reconstruction area.

Hereinafter, a drawing method of the virtual wave front will be described in detail. In FIG. 3A, a matching material 14 is filled between the first holding plate 1 and the surface (each element 2a) of the probe 2. Water or plant-derived oil such as castor oil and jojoba oil are suitable for the matching material 14.

In the description below, regarding reference characters, c is a sound speed, z is a distance in a depth direction, x is a distance in a direction on the scanning surface of the probe 2, and $\theta$ is a refraction angle. Further, regarding subscript characters, M means the matching material 14, P means the first holding plate 1, and B means the subject.

First, a method for drawing a virtual wave front R (a) in the circular back projection indicated by a dashed line from the time $\tau$ will be described. Here, $\alpha$ is a parameter indicating a direction of drawing.

Figure 3B:
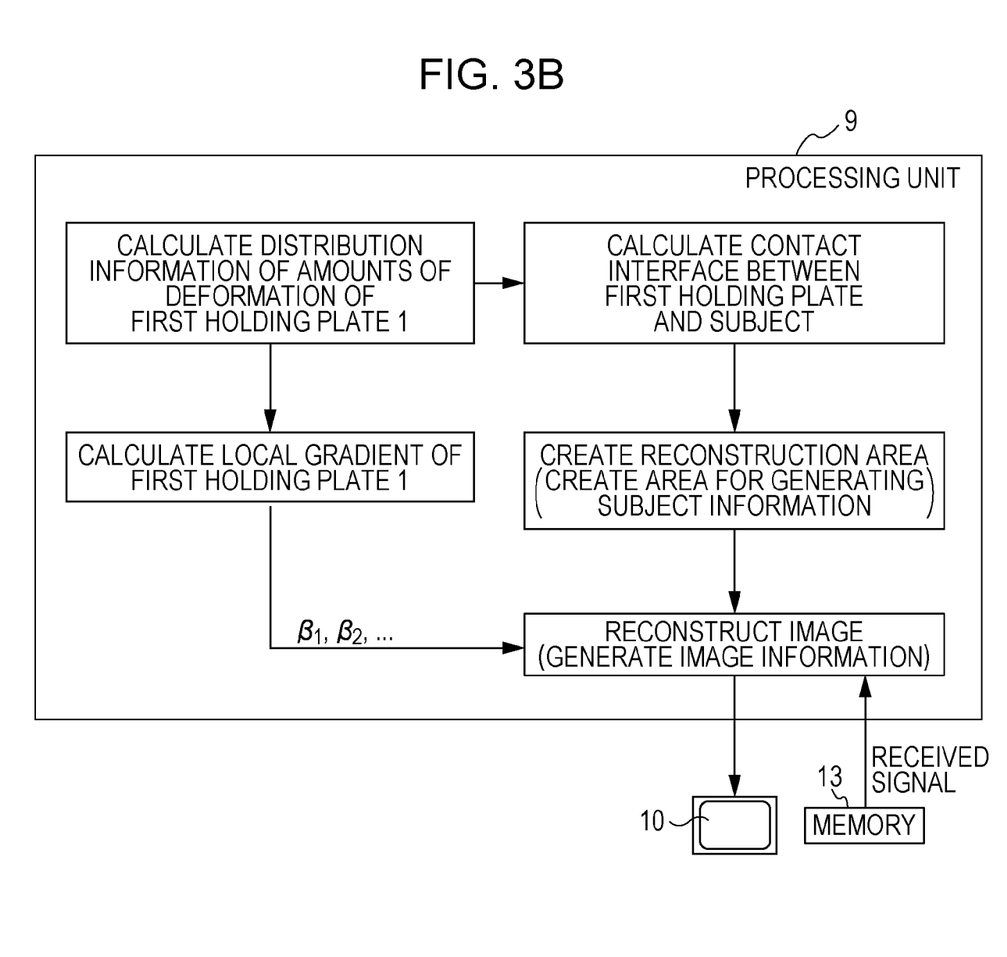

It is possible to calculate local positions of the first holding plate 1 and angles $\beta_1$ and $\beta_2$ between the scanning surface of the probe 2 and a normal direction at the positions from the accurate reconstruction area acquired using the distribution information of amounts of deformation of the first holding plate 1 when the subject is held (see FIG. 3B). The image reconstruction is performed as described below.

The following formula can be obtained from FIG. 3A.

$$x_M = c_M \tau_M \cos \alpha$$

Here, $c_M \tau_M$ can be geometrically calculated by $\alpha$ from a distance between the scanning surface of the probe 2 and the first holding plate 1 and the flatness information of the first holding plate 1.

$$x_M = c_M \tau_M \sin(\theta_M - \beta_1)$$

is established. Therefore, a refraction angle $\theta_M$ in the matching material 14 can be obtained by the following formula.

$$\theta_M = \sin^{-1}(\cos \alpha) + \beta_1$$

A refraction angle $\theta_P$ in the first holding plate 1 and a refraction angle $\theta_B$ in the subject are respectively calculated from the Snell's law as described below.

$$\theta_P = \sin^{-1}(c_P \sin \theta_M/c_M) \quad \theta_B = \sin^{-1}(c_B \sin \theta_P/c_P)$$

is established. Next, when the thickness of the first holding plate is $t_P$, $$c_P \tau_P = t_P/\cos \theta_P$$

is established.

Therefore, $t_P/c_P\tau_P = \cos \theta_P$, so that $x_P = c_P \tau_P \sin(\theta_P - \beta_2) = t_P \sin(\theta_P - \beta_2)/\cos \theta_P$ can be obtained.

$\tau = \tau_B + \tau_P + \tau_M$, so that $\tau_B = \tau - (\tau_P + \tau_M)$. Therefore, the following formula is established.

$$x_B = c_B \tau_B \sin(\theta_B - \beta_2) = c_B\{\tau - (\tau_P + \tau_M)\} \sin(\theta_B - \beta_2)$$

Similarly, the following formula can be obtained in the depth direction.

$$z_M = c_M \tau_M \cos(\theta_M - \beta_1) z_P = c_P \tau_P \cos(\theta_P - \beta_2) zB = c_B \tau_B \cos(\theta_B - \beta_2)$$

As described above, the virtual wave front R (α) in the circular back projection can be drawn from the time τ in which an elastic wave emitted from a certain point in the subject reaches one element 2a of the probe 2.

As described above, the time τ in which an elastic wave emitted from the subject reaches one element 2a of the probe 2 is a time period from when the light source of the illumination system 7 emits light to when one element 2a receives the elastic wave. When virtual wave fronts are drawn for other elements in the same manner, the wave fronts overlap at the generation source of the elastic wave, so that the generation source can be identified. The subject information (absorption coefficient distribution, oxygen saturation distribution, and the like) can be generated as an image by plotting information values such as absorption coefficients and oxygen saturation values based on the signal of the elastic wave from the generation source in the reconstruction area. The signal of the elastic wave from the generation source is received by one or more elements, so that information values based on the signal can be obtained by appropriately processing the signal (for example, performing addition processing).

Although the image reconstruction by the circular back projection is described as the method for generating the image information, the method for generating the image information is not limited to this. Other image information calculation methods can be applied if the Snell's law is used and the geometrical calculation as described in FIG. 3 is performed.

FIG. 3A is a schematic diagram that is shown two-dimensionally and the refraction correction method of the elastic wave is described on the basis of FIG. 3A. However, this method can be applied to actual three-dimensional refraction correction including a direction perpendicular to the page of FIG. 3A.

Although, in FIG. 3A, a configuration of three layers including the matching material 14, the first holding plate 1, and the subject is described, it is not limited to this. For example, the refraction layer may be formed by only the holding plate without using the matching material. Or, even if refraction layers of the elastic wave are added, the above method can be applied.

As described above, even when the holding member is deformed outward, it is possible to reduce degradation of the resolution by performing the refraction correction of the elastic wave using the accurate reconstruction area created in the first or the second embodiment.

The above method can be applied to a configuration in which an ultrasonic wave is transmitted from an ultrasonic wave transmission source and an ultrasonic wave reflected from a certain position in the subject is received. In this case, the processing unit processes the signal of the ultrasonic wave from the certain position in the subject by basically the same principle.

Here, the origin of the time of the received signal (a time point when the ultrasonic wave from the transmission source reaches the certain position) can be calculated because the position of the transmission source in the reconstruction area, the path of the ultrasonic wave from the transmission source to the certain position, the sound speeds in each portion, the transmission time at the transmission source, and the like are known.

Therefore, even when the ultrasonic pulse-echo technique is used, the processing unit accurately plots the information values in the reconstruction area by the above method on the basis of the received signal at the probe, so that the subject information (distribution in which differences of acoustic impedances are reflected, or the like) can be acquired.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2011-058661 filed Mar. 17, 2011, which is hereby incorporated by reference herein in its entirety.

What is claimed is:

1. A subject information acquisition apparatus comprising:
a first holding member configured to hold a subject;
a probe configured to receive an elastic wave from the subject through the first holding member and generate an output signal;
a first holding member deformation amount measuring unit configured to measure an amount of deformation of the first holding member; and
a processing unit configured to create an area for generating subject information by using the amount of deformation of the first holding member and position information of the first holding member deformation amount measuring unit and generate an information value of subject information corresponding to the area for generating subject information by using the signal outputted by the probe.

2. The subject information acquisition apparatus according to claim 1, further comprising:
a second holding member configured to enclose the subject between the second holding member and the first holding member; and
a second holding member deformation amount measuring unit configured to measure an amount of deformation of the second holding member,
wherein the processing unit creates the area for generating subject information by using the amount of deformation of the first holding member, position information of the first holding member deformation amount measuring unit, the amount of deformation of the second holding member, position information of the second holding member deformation amount measuring unit, and member-to-member distance information between the first holding member and the second holding member.

3. The subject information acquisition apparatus according to claim 2, further comprising:
a compression mechanism configured to drive the first holding member or the second holding member,
wherein the compression mechanism includes a member-to-member distance measuring unit configured to measure the member-to-member distance information between the first holding member and the second holding member.

4. The subject information acquisition apparatus according to claim 1, further comprising a probe scanning mechanism configured to cause the probe to scan along a surface of the first holding member.

5. The subject information acquisition apparatus according to claim 4, wherein
the probe scanning mechanism includes the first holding member deformation amount measuring unit, and
the processing unit acquires position information of the first holding member deformation amount measuring unit based on a scanning position of the probe scanning mechanism.

6. The subject information acquisition apparatus according to claim 1, wherein the processing unit calculates a local gradient of the first holding member from the area for generating subject information, and the processing unit calculates refraction of an elastic wave generated in an interface between the subject and the first holding member according to Snell's law and identifies a position in the area for generating subject information from which an elastic wave that generates a signal received by the probe is transmitted.

7. The subject information acquisition apparatus according to claim 1, further comprising:

a matching material filled between the first holding member and the probe, wherein the processing unit calculates refraction of an elastic wave generated in an interface between the first holding member and the matching material according to Snell's law and identifies a position in the area for generating subject information from which an elastic wave that generates a signal received by the probe is transmitted.

8. The subject information acquisition apparatus according to claim 1, wherein the first holding member deformation amount measuring unit is attached directly to a plurality of positions on the first holding member or a first fixing member that fixes the first holding member.

9. The subject information acquisition apparatus according to claim 1, wherein the second holding member deformation amount measuring unit is attached directly to a plurality of positions on the second holding member or a second fixing member that fixes the second holding member.

10. A subject information acquisition method comprising:

a step of receiving an elastic wave from a subject through a first holding member by a probe and outputting a signal;

a step of acquiring, by a first holding member deformation amount measuring unit, distribution information of amounts of deformation of the first holding member;

a step of creating an area for acquiring subject information based on the distribution information of amounts of deformation of the first holding member and position information of the first holding member deformation amount measuring unit; and a step of generating an information value of subject information corresponding to the area for acquiring subject information from the signal outputted by the probe.

* * * * *